United States Patent [19]

Howe et al.

[11] 4,308,391

[45] Dec. 29, 1981

[54] 2-AMINO-4-SUBSTITUTED-THIAZOLECAR-BOXYLIC ACIDS AND THEIR DERIVATIVES

[75] Inventors: Robert K. Howe, Bridgeton; Len F. Lee, Maryland Heights, both of Mo.

[73] Assignee: Monsanto Company, St. Louis, Mo.

[21] Appl. No.: 80,752

[22] Filed: Oct. 1, 1979

[51] Int. Cl.$^3$ .......................................... C07D 277/18
[52] U.S. Cl. ........................................ 548/194; 71/90
[58] Field of Search ................. 71/90; 548/184, 194, 548/188

[56] References Cited

U.S. PATENT DOCUMENTS

| | | | |
|---|---|---|---|
| 2,726,237 | 12/1955 | Towne et al. | 260/158 |
| 2,726,247 | 12/1955 | Towne et al. | 260/306.8 |
| 3,505,055 | 4/1970 | von Schmeling et al. | 71/90 |
| 3,547,917 | 12/1970 | Kulka et al. | 260/247.1 |
| 3,725,427 | 4/1973 | Harrison et al. | 260/302 R |
| 3,775,425 | 11/1973 | Bosshard et al. | 71/90 |
| 3,796,800 | 3/1974 | Ariyan et al. | 424/270 |
| 3,874,873 | 4/1975 | Volpe et al. | 71/90 |
| 3,879,531 | 4/1975 | Ariyan et al. | 424/270 |
| 4,115,095 | 9/1978 | Franz et al. | 71/90 |

FOREIGN PATENT DOCUMENTS 658353  1/1936  Fed. Rep. of Germany .

OTHER PUBLICATIONS

CA vol. 19 Pt 2 (1925) p. 2931.
CA vol. 40 Pt 2 (1946) pp. 4056-4062.
CA vol. 42 Pt. 1 (1948) p. 2969.
CA vol. 54 22576 (1960).
CA vol. 58 4534 (1963).
Clarke et al., J. Chem. Soc. (B) (1966) pp. 339-343.
Garaway Pestic. Science vol. 5 (1974) pp. 185-188.
Wohmann, M., Die Diazoverbindungen der Thiazolreihe and Ihre Reactionen, CZ 1891 #1 pp. 68-69.

*Primary Examiner*—Nicholas S. Rizzo
*Attorney, Agent, or Firm*—Patricia A. Coburn; Donald W. Peterson

[57] ABSTRACT

2-Amino-4-substituted-5-thiazolecarboxylic acids and derivatives thereof, are intermediates for the preparation of 2-substituted-4-substituted-5-thiazolecarboxylic acid derivatives which are herbicidal safeners.

8 Claims, No Drawings

2-AMINO-4-SUBSTITUTED-THIAZOLECARBOXYLIC ACIDS AND THEIR DERIVATIVES

This invention relates to novel 2-amino-4-substituted-5-thiazolecarboxylic acids and derivatives thereof which are intermediates for the preparation of 2,4,5-substituted thiazoles which are effective herbicidal safening agents. Such compounds and their use as herbicidal safeners are described in co-pending Ser. No. 905,682 and Ser. No. 906,183, now U.S. Pat. No. 4,199,506 also Application Ser. No. 080,751, filed Oct. 1, 1979 titled "2-Chloro-4,5-Disubstituted Thiazoles Useful As Herbicidal Safeners" by Robert K. Howe and Len F. Lee.

BACKGROUND OF THE INVENTION

Herbicides are very useful for controlling certain weeds in the presence of growing crops. However, many herbicides injure certain crop plants slowing growth and development at rates necessary to kill or stunt weeds. Accordingly, some herbicides cannot be used for controlling weeds in the presence of certain crops. Obviously, a safening agent which consists of a chemical compound that is to be used to treat either the seed of the crop plant, the crop plant locus, or the crop plant itself, to reduce the injury due to application of a herbicide without a corresponding reduction of herbicidal action on weeds, is quite beneficial. The compounds of the present invention can be used to prepare certain 2-substituted-4-substituted 5-thiazolecarboxylic acids and derivatives thereof, which are effective herbicidal safeners as disclosed in co-pending Ser. No. 905,682 and Ser. No. 906,183, and Application Ser. No. 080,751, filed Oct. 1, 1979 titled "2-Chloro-4,5-Disubstituted Thiazoles Useful As Herbicidal Safeners" by Robert K. Howe and Len F. Lee, the disclosures of which are herein incorporated by reference.

DESCRIPTION OF THE INVENTION

The present invention relates to compounds having the formula:

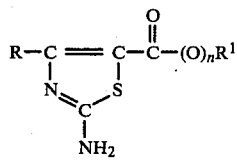

wherein n is zero or one; R is selected from the group consisting of alkyl having 3 to 9 carbon atoms, cycloalkyl having 3 to 8 carbon atoms, halo(lower)alkyl, and

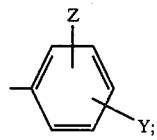

Y and Z are indepdendently selected from the group consisting of hydrogen, halogen, trifluoromethyl and lower alkyl; when n is one, $R^1$ is selected from the group consisting of hydrogen, alkyl having 1 to 10 carbon atoms, lower alkenyl, lower alkynyl, lower alkoxy lower alkyl, halo(lower)alkyl, benzyl, phenyl and phenyl substituted by one or two members selected from the group consisting of halogen, lower alkyl and trifluoromethyl; when n is zero, $R^1$ is $-NR_2R_3$ where $R_2$ and $R_3$ are independently equal to lower alkyl; provided that when n is one and $R^1$ is hydrogen, Z and Y cannot both equal hydrogen; further provided that when n is one $R^1$ is alkyl containing 1 to 10 carbon atoms or benzyl, R cannot equal trifluoromethyl.

As used herein, the terms "lower alkyl", "lower alkoxy", "lower alkenyl" and "lower alkynyl" are understood to include alkyl, alkoxy, alkenyl and alkynyl groups having up to five carbon atoms, inclusive.

The terms "alkyl", "alkoxy", "alkenyl" and "alkynyl" are understood to include branched and unbranched groups. When $R^1$ is lower alkenyl, allyl is preferred. When $R^1$ is lower alkynyl, propargyl is preferred. "Halogen" includes bromine, chlorine, fluorine and iodine.

"Cycloalkyl" containing 3 to 8 compounds includes cyclopropyl, cyclobutyl, cyclopentyl, cyclohexyl, cycloheptyl and cyclooctyl. Preferred for use herein are those cycloalkyls containing 5 to 7 carbon atoms, cyclohexyl is most preferred.

The term "halo(lower)alkyl" is understood to mean those alkyl moieties having up to five carbon atoms wherein at least one hydrogen atom has been replaced by a halogen atom. Specifically included are those alkyl moieties in which all of the hydrogen atoms have been replaced by halogen atoms, such as trifluoromethyl.

The following may be mentioned as examples of the 2-amino-4-substituted-5-thiazolecarboxylate which are valuable as intermediates in the preparation of herbicidal antidotes:

ethyl 2-amino-4-isopropyl-5-thiazolecarboxylate,
propyl 2-amino-4-ethyl-5-thiazolecarboxylate,
ethyl 2-amino-4-t-butyl-5-thiazolecarboxylate,
ethyl 2-amino-4-(p-fluorophenyl)-5-thiazolecarboxylate,
ethyl 2-amino-4-(p-chlorophenyl)-5-thiazolecarboxylate,
ethyl 2-amino-4-(o-chlorophenyl)-5-thiazolecarboxylate,
ethyl 2-amino-4-(m-tolyl)-5-thiazolecarboxylate,
ethyl 2-amino-4-(α,α,α-trifluoro-m-tolyl)-5-thiazolecarboxylate,
ethyl 2-amino-4-cyclohexyl-5-thiazolecarboxylate,
2,2,2-trichloroethyl 2-amino-4-trifluoromethyl-5-thiazolecarboxylate,
2-butoxyethyl 2-amino-4-trifluoromethyl-5-thiazolecarboxylate,
phenyl 2-amino-4-trifluoromethyl-5-thiazolecarboxylate,
p-chlorophenyl 2-amino-4-trifluoromethyl-5-thiazolecarboxylate,
propargyl 2-amino-4-trifluoromethyl-5-thiazolecarboxylate,
allyl 2-amino-4-trifluoromethyl-5-thiazolecarboxylate,
N,N-diethyl-2-amino-4-trifuloromethyl-5-thiazolecarboxamide,
N,N-diethyl-2-amino-4-isopropyl-5-thiazolecarboxamide and
N,N-diethyl-2-amino-4-chloromethyl-5-thiazolecarboxamide.

The 2-amido-4-substituted-5-thiazolecarboxylic acids and derivatives of the foregoing formula may be prepared utilizing the following procedures. For purposes of clarification, these procedures are summarized by Schemes I and II.

Compounds of the present invention wherein n is equal to one are prepared according to Scheme I.

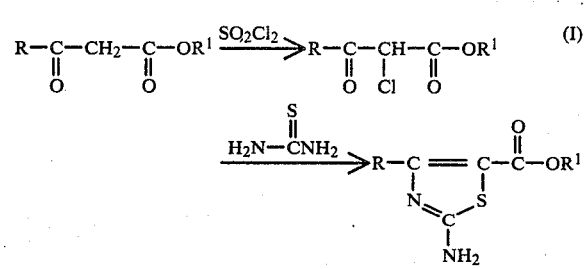

In accordance with the above reaction scheme, ketoesters in chloroform are added dropwise to one equivalent of sulfuryl chloride. The reaction mixture is held at reflux for a number of hours and the chloroform removed under reduced pressure. An equimolar portion of the resultant 2-chloro-3-ketoester is added to thiourea in ethanol and held at reflux for 16–20 hours. Ethanol is then removed under reduced pressure and the residue neutralized with sodium bicarbonate solution to give 2-amino-4-substituted-5-thiazolecarboxylic acids or esters.

The preparation of compounds of the present invention wherein n is equal to zero and $R^1$ is equal to $-NR_2R_3$ is illustrated by Scheme II:

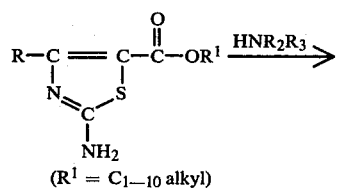

Further details of the compounds of the present invention and their preparation are found in the following non-limiting examples.

EXAMPLE 1

Preparation of Ethyl 2-Amino-4-Ethyl-5-Thiazolecarboxylate

Ethyl 2-chloro-3-oxo-pentanoate was prepared from ethyl 3-oxo-pentanoate and sulfuryl chloride utilizing the procedure of Bankowski et al, *Rocz. Chem.*, Volume 49, Page 1899 (1971). A mixture of 9.2 g (0.0515 mole) of ethyl 2-chloro-3-oxo-pentanoate, 3.92 g (0.0515 mole) of thiourea and 30 ml. of ethanol was held at reflux for 17 hours. Ethanol was removed under reduced pressure and the residue was treated with 300 ml. of saturated sodium bicarbonate solution. The solid precipitate was collected to give 11.2 g of white solid, m.p. 165°–170° C. which was recrystallized from ethanol to give 7.7 g (75%) of ethyl 2-amino-4-ethyl-5-thiazolecarboxylate as colorless prisms, m.p. 177°–179° C.

Anal. Calc'd. for $C_8H_{12}N_2O_2S$: C, 47.97; H, 6.04; N, 13.99; Found: C, 47.92; H, 6.04; N, 14.00.

EXAMPLE 2

Preparation of Ethyl 2-Amino-4-t-Butyl-5-Thiazolecarboxylate

Utilizing ethyl 2-chloro-4,4-dimethyl-3-oxo-pentanoate and the procedure of Example 1, ethyl 2-amino-4-t-butyl-5-thiazolecarboxylate was prepared, m.p. 99.0°–100.0° C.

Anal. Calc'd. for $C_{10}H_{16}N_2O_2S$: C, 52.60; H, 7.06; N, 12.27; Found: C, 52.66; H, 7.06; N, 12.21.

EXAMPLE 3

Preparation of Ethyl 2-Amino-4-(p-Fluorophenyl)-5-Thiazolecarboxylate

A mixture of 10.5 g (0.05 mole) of ethyl p-fluorobenzoylacetate, 6.7 g (0.05 mole) of sulfuryl chloride and 30 ml. of chloroform was held at reflux for 18 hours and cooled. The chloroform solution was washed with water, dried (MgSO$_4$) and concentrated under reduced pressure. The residue was distilled to give 10.8 g (88%) of ethyl 2-chloro-(p-fluoro)-benzoylacetate as an oil. A mixture of 10.8 g (0.441 mole) of ethyl 2-chloro-(p-fluoro)-benzoylacetate, 3.36 g (0.0441 mole) of thiourea, 20 ml. of water and 10 ml. of ethanol was held at reflux for 3 hours. Ethanol was removed under reduced pressure. The residue was made basic with saturated sodium bicarbonate. The solid was filtered, washed with water and recrystallized from ethanol to give 8.9 g (76%) of ethyl 2-amino-4-(p-fluorophenyl)-5-thiazolecarboxylate as white prisms, m.p. 205°–208° C.

Anal. Calc'd for $C_{12}H_{11}FN_2O_2S$: C, 54.11; H, 4.16; N, 10.52; Found: C, 54.12; H, 4.16; N, 10.52.

EXAMPLE 4

Preparation of Ethyl 2-Amino-4-p-Chlorophenyl-5-Thiazolecarboxylate

To a cold (5° C.) vigorously stirred mixture of 121.87 g (0.936 mole) of ethyl acetoacetate, 314 ml. of benzene and 626 ml. of water was added 41.25 ml. of 33% sodium hydroxide. To the above mixture was added simultaneously, in two dropping funnels, 177.0 g (1.01 mole) of p-chlorobenzoyl chloride and 188.8 ml. of 33% sodium hydroxide in 2 hours. The reaction mixture became pasty. The reaction mixture was heated at 35° C. for 1 hour, cooled and filtered to give 170.0 g of sodium salt of ethyl 2-benzoylacetoacetate. Part (150 g) of this salt was added to a mixture of 39.0 g (0.729 mole) of ammonium chloride and 78 ml. of concentrated ammonium hydroxide in 780 ml. of water. The mixture was stirred at 40°–50° C. for 3 hours and cooled in an ice bath. The precipitate was filtered to give 115.5 g of yellow solid which was Kugelrohr distilled to give 76.0 g (38% based on ethyl acetoacetate) of crude ethyl p-chlorobenzoylacetate. A mixture of 40.0 g (0.175 mole) of crude ethyl p-chlorobenzoylacetate, 24.2 g (0.18 mole) of sulfuryl chloride and some chloroform was held at reflux for 6 hours, cooled and concentrated to give 49.0 g of crude ethyl 2-chloro-p-chlorobenzoylacetate. A mixture of 46.0 g (0.174 mole) of crude ethyl 2-chloro-p-chlorobenzoylacetate, 13.25 g (0.174 mole) of thiourea, and 174 ml. of ethanol was held at reflux for 2 hours and cooled. The precipitate was filtered and neutralized with saturated sodium bicarbonate. The insoluble material was filtered to give 37.0 g (80%) of ethyl 2-amino-4-p-chlorophenyl-5-thiazolecarboxylate, m.p. 198°–200° C.

Anal. Calc'd for $C_{12}H_{11}ClN_2O_2S$: C, 50.96; H, 3.92; N, 9.90; Found: C, 50.88; H, 3.93; N, 9.90.

EXAMPLE 5

Preparation of Ethyl
2-Amino-4-(o-Chlorophenyl)-5-Thiazolecarboxylate

To a cold (5° C.) mixture of 55.0 g (0.423 mole) of ethyl acetoacetate, 70 ml. of benzene, 18.3 ml. of 33% sodium hydroxide, and 141 ml. of water was added simultaneously with vigorous stirring 80.0 g (0.457 mole) of o-chlorobenzoyl chloride and 76 ml. of 33% sodium hydroxide in 1 hour. The aqueous solution of the sodium salt of ethyl o-chlorobenzoylacetoacetate was stirred with 22.5 g (0.424 mole) of ammonium chloride for 18 hours. The aqueous solution was then saturated with 25.0 g of sodium chloride. At this moment, some precipitate formed which was filtered. The analysis indicated this material was mainly the sodium salt of ethyl o-chlorobenzoylacetoacetate. The sodium salt and the aqueous filtrate were combined and acidified with dilute hydrochloric acid. The oil which separated was extracted with ether. The ether solution was dried (MgSO4) and concentrated under reduced pressure. The residue was Kugelrohr distilled to give 30.0 g of oil which contained mainly ethyl o-chlorobenzoylacetoacetate. This material was stirred with a mixture of 7.2 g of ammonium chloride, 14 ml. of concentrated ammonium hydroxide and 150 ml. of water and worked up as described in Example 4 to give 16.6 g (15%) of crude ethyl o-chlorobenzoylacetate which was about 92% pure. A mixture of 15.0 g. (0.065 mole) of ethyl o-chlorobenzoylacetate, 9.5 (0.070 mole) of sulfuryl chloride and 20 ml. of chloroform was held at reflux for 6 hours and concentrated to give 17.3 g of crude ethyl 2-chloro-o-chlorobenzoylacetate. A mixture of 17.0 g (0.065 mole) of ethyl 2-chloro-o-chlorobenzoylacetate, 4.94 g (0.065 mole) of thiourea and 65 ml. of ethanol was held at reflux for 2 hours and worked up as described in Example 4 to give 15.0 g of solid, m.p. 114°–136° C. which was recrystallized twice from ethanol to give 5.8 g (31%) of ethyl 2-amino-4-(o-chlorophenyl)-5-thiazolecarboxylate, m.p. 165°–166° C.

Anal. Calc'd for $C_{12}H_{11}ClN_2O_2S$: C, 50.96; H, 3.92; N, 9.90; Cl, 12.54. Found: C, 50.96; H, 3.96; N, 9.91; Cl, 12.54.

EXAMPLE 6

Preparation of Ethyl
2-Amino-4-(m-Tolyl)-5-Thiazolecarboxylate

To a cold (5° C.) mixture of 137.5 g (1.05 mole) of ethyl acetoacetate, 175 ml. of benzene, 325 ml. of water, and 45.8 ml. of 33% sodium hydroxide was added simultaneously 221.05 g (1.430 mole) of m-toluoyl chloride and 190 ml. of 33% sodium hydroxide as described in Example 4. The aqueous solution of sodium salt of ethyl m-toluoylacetoacetate was stirred with 56.3 g of ammonium chloride overnight and worked up as described in Example 4 to give 38.0 g (17%) of crude ethyl m-toluoylacetate after a Kugelrohr distillation (95°–98° C.) at 0.05 mm Hg). A mixture of 20.6 g (0.1 mole) of crude ethyl m-toluoylacetate, 13.6 g (0.105 mole) of sulfuryl chloride, and 30 ml. of chloroform was held at reflux for 6 hours and worked up as described in Example 4 to give 25.0 g of ethyl 2-chloro-m-toluoylacetate, which was used directly as described below. A mixture of 22.5 g (0.1 mole) of ethyl 2-chloro-m-toluoylacetate, 7.6 g (0.11 mole) of thiourea and 100 ml. of ethanol was held at reflux for 2 hours and worked up as described in Example 4 to give 23.0 g of solid, which was recrystallized from ethanol to give 11.6 g (44%) of ethyl 2-amino-4-(m-tolyl)-5-thiazolecarboxylate, m.p. 185°–187° C.

Anal. Calc'd. for $C_{13}H_{14}N_2O_2S$: C, 59.52: H, 5.38; N, 10.68. Found: C, 59.55; H, 5.42; N, 10.68.

EXAMPLE 7

Preparation of Ethyl
2-Amino-4-Isopropyl-5-Thiazolecarboxylate

Utilizing the procedure of Example 1, a mixture of 1.97 g (0.01 mol) of ethyl 2-chloro-4-methyl-pentanoate, 0.76 g (0.01 mol) of thiourea and 30 ml of ethanol was held at reflux for 18 hours. Ethanol was removed under reduced pressure. The residue was crystallized from hexane. The solid precipitates were dissolved in ether. The ether solution was washed with water, dried over magnesium sulfate and concentrated under reduced pressure. The residue was recrystallized from benzene-ether to give 0.85 g (39.6%) of ethyl 2-amino-4-isopropyl-5-thiazolecarboxylate, m.p. 173°–176° C.

Anal. Calc'd. for $C_9H_{14}N_2O_2S$: C, 50.44; H, 6.58; N, 6.58; Found: C, 50.47; H, 6.61; N, 13.07.

Compounds of the present invention which are prepared according to the procedure described in Scheme II which may be mentioned, include, but are not limited to:

N,N-diethyl 2-amino-4-trifluoromethyl-5-thiazolecarboxamide,

N,N-diisopropyl-2-amino-4-isopropyl-5-thiazolecarboxamide,

N,N-di-tert-butyl-2-amino-4-phenyl-5-thiazolecarboxamide,

N,N-diethyl-2-amino-4-cyclohexyl-5-thiazolecarboxamide,

N,N-dipropyl-2-amino-4-chloromethyl-5-thiazolecarboxamide, and

N,N-di-n-butyl-2-amino-4-trimethoxymethyl-5-thiazolecarboxamide.

In accordance with the novel aspects of the present invention, the 2-amino-4-substituted-thiazolecarboxylates are intermediates in the preparation of certain 2-substituted-4-substituted-thiazole carboxylates which have been found to be effective in reducing herbicidal injury to selected crop plants due to application of herbicides.

Safening agents having the formula

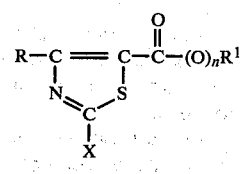

where R and $R^1$ have the meanings previously described and where X is equal to chloro, bromo, fluoro or iodo, may be prepared utilizing compounds of the present invention according to the following procedure:

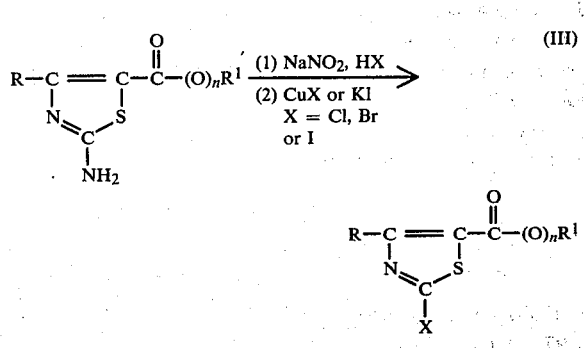

In accordance with the above reaction scheme, a solution of the 2-aminothiazole compounds of the present invention is diazotized at −50° to 30° C. with sodium nitrite. The resulting diazonium salt solution is poured into an appropriate cuprous halide or potassium iodide solution. After gas evolution has subsided, the reaction mixture is extracted with ether. The ether extract is dried, concentrated and the residue purified by Kugelrohr distillation at reduced pressure or by chromatography.

In yet another aspect of the present invention, safening agents of the formula

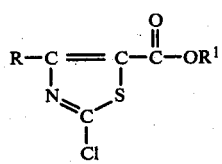

where R and R¹ are as previously described, and may be prepared as illustrated in Scheme IV:

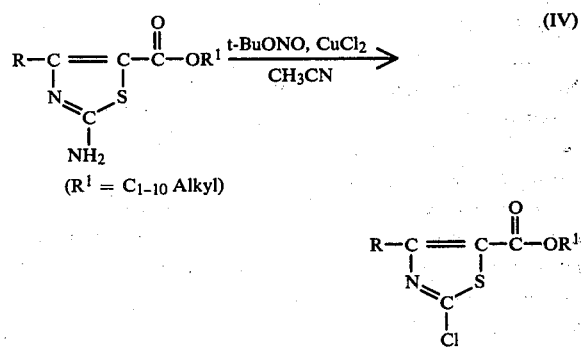

In accordance with the process illustrated by the above reaction, to an equimolar mixture of t-butyl nitrite and cupric chloride in acetonitrile is added an approximately equimolar amount of the 2-aminothiazole starting material. The reactants are usually admixed at room temperature, i.e., about 25° C. However, higher or lower temperatures can be employed, the temperature not being critical.

The separation of the resulting reaction product from the reaction mixture is readily accomplished by conventional means. For example, the reaction mixture may be filtered to directly obtain the product or the filtrate may be triturated with a suitable volume of 6 N HCl. Thereafter, the mixture is extracted with a suitable organic solvent, as for example, ether. The extract is dried and concentrated by Kugelrohr distillation.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound of the formula

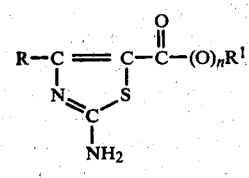

wherein n is zero or one; R is alkyl having 3 to 9 carbon atoms, cycloalkyl having 3 to 8 carbon atoms, halo(lower)alkyl, or

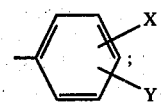

X and Y independently equal hydrogen; halogen, trifluoromethyl or lower alkyl; when n is one R¹ is hydrogen, alkyl having 1 to 10 carbon atoms, lower alkenyl, lower alkynyl, lower alkoxy lower alkyl, halo(lower)alkyl, benzyl, phenyl or phenyl substituted by one to two halogen, lower alkyl or trifluoromethyl moieties; when n is zero R¹ is —NR₂R₃ where R₂ and R₃ independently equal lower alkyl; provided that when n is one and R¹ is hydrogen, X and Y cannot both equal hydrogen; further provided that when n is one and R¹ is alkyl containing 1 to 10 carbon atoms or benzyl, R cannot equal trifluoromethyl.

2. A compound according to claim 1 wherein n is one.

3. A compound according to claim 2 wherein R₁ is alkyl containing 1 to 10 carbon atoms, lower alkenyl, lower alkynyl or lower alkoxy(lower)alkyl.

4. A compound according to claim 3 wherein R is halo(lower)alkyl, or

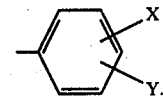

5. A compound according to claim 1 wherein n is zero.

6. A compound according to claim 5 wherein R is alkyl having 3 to 9 carbon atoms, cycloalkyl having 3 to 8 carbon atoms, halo(lower)alkyl.

7. A compound according to claim 6 wherein R is trifluoromethyl.

8. A compound according to claim 1 which is ethyl-2-amino-4-t-butyl-5-thiazolecarboxylate.

* * * * *